United States Patent [19]

Vandersput

[11] 4,195,187
[45] Mar. 25, 1980

[54] PROCESS FOR SELECTIVELY OXIDIZING ISOBUTYLENE TO METHACROLEIN AND METHACRYLIC ACID

[75] Inventor: Thomas H. Vandersput, Gillette, N.J.

[73] Assignee: Celanese Corporation, New York, N.Y.

[21] Appl. No.: 832,712

[22] Filed: Sep. 12, 1977

[51] Int. Cl.² .................... C07C 45/04; C07C 51/32; C07C 57/04
[52] U.S. Cl. .................... 562/545; 252/435; 252/437; 252/439; 252/455 R; 252/456; 252/458; 252/462; 252/467; 252/469; 260/604 R; 562/547
[58] Field of Search .................... 562/545, 547; 260/604 R; 252/435, 437, 439, 455 R, 456, 458, 462, 467, 469

[56] References Cited

U.S. PATENT DOCUMENTS

| 3,554,928 | 1/1971 | Eden | 562/547 |
| 3,879,453 | 4/1975 | Ono et al. | 562/547 |

*Primary Examiner*—Vivian Garner
*Attorney, Agent, or Firm*—Kenneth A. Genoni

[57] ABSTRACT

This invention provides a process for preparing an improved selective oxidation catalyst consisting of a highly compressed mixture of metal oxides in which the atomic ratio of elements varies between about 0.3 and 2.4 atoms selected from phosphorus, manganese, germanium, zirconium, tin, tellurium, cerium and hafnium, and between about 0.4 and 3.6 atoms selected from titanium, vanadium, niobium, antimony and tantalum, per twelve atoms of molybdenum.

4 Claims, No Drawings

PROCESS FOR SELECTIVELY OXIDIZING ISOBUTYLENE TO METHACROLEIN AND METHACRYLIC ACID

BACKGROUND OF THE INVENTION

There is extensive prior art literature describing methods for selective oxidation of olefins to alpha, beta-unsaturated aldehydes and carboxylic acids. An important aspect of selective oxidation studies have involved conversion of isobutylene to methacrolein and methacrylic acid. The yields of methacrolein obtained with known catalyst systems have generally been lower than the yields achieved in the selective oxidation of propylene to acrolein.

There is continuing development effort in progress on new catalyst systems for improving yield and efficiency of isobutylene oxidation to methacrolein and methacrylic acid.

Of primary importance, is the achievement of the highest possible single-pass yield of useful products, because it is generally uneconomical to recover and recycle unreacted isobutylene. However, as the conversion rate of isobutylene is increased, the quantity of undesirable products produced, such as carbon dioxide, carbon monoxide and acetic acid also increases because of oxidative decomposition. This causes a decrease in the selectivity to methacrolein and methacrylic acid. In addition to the requirement for high single-pass yields of product, the catalyst system must also have a sufficient activity as well as possess a sufficient lifetime so as to be useable in industrial applications.

U.S. Pat. No. 3,879,453 describes an improved process for producing methacrolein and methacrylic acid by contacting isobutylene with molecular oxygen in vapor phase in the presence of a new catalyst system. The catalyst consists of a mixture of solid metal oxides corresponding to the empirical formula $Sb_aV_bMo_cTe_dW_eM_fO_g$, wherein M represents at least one element selected from the group consisting of bismuth, thallium and uranium, and wherein the atomic ratio of elements in the formula is such that $a=10$, $b=0.1-10$, $c=0.4-15$, $d=0.1-10$, $e=0-2$ and $g=16-127$.

U.S. Pat. No. 3,939,208 discloses an improved process for producing methacrolein which involves contacting isobutylene with oxygen or oxygen-containing gaseous mixtures in vapor phase in the presence of a new catalyst composition corresponding to the formula $Me_vTe_xCe_yMo_{12}O_z$, wherein Me is Na, K, Li, Rb and/or Cs, $v=0.3-18$, $x=0.3-24$, $y=0.3-21$ and z corresponds to the quantity of oxygen bound to the other elements.

There remains a need for improved selective oxidation systems adapted for the conversion of isobutylene to methacrolein and methacrylic acid with high single pass conversion and efficiency.

Accordingly, it is an object of this invention to provide a method for preparing an improved selective oxidation catalyst.

It is another object of this invention to provide a novel molybdate catalyst adapted for selective oxidation of olefins to alpha, beta-unsaturated aldehydes and carboxylic acids.

It is a further object of this invention to provide an improved process for selectively oxidizing isobutylene to methacrolein and methacrylic acid in high single-pass yield.

Other objects and advantages shall become apparent from the accompanying description and examples.

DESCRIPTION OF THE INVENTION

One or more objects of the present invention are accomplished by the provision of a process for preparing an improved selective oxidation catalyst which comprises (1) preparing an aqueous solution of ammonium molybdate; (2) dissolving in the said aqueous solution at least one water-soluble compound of an element selected from phosphorus, manganese, germanium, zirconium, tin, tellurium, cerium and hafnium; (3) admixing with said aqueous solution at least one water-soluble compound of a metal selected from titanium, vanadium, niobium, antimony, and tantalum to form a suspension; (4) removing the aqueous phase of said suspension and recovering a solid catalyst precursor; (5) heating said solid catalyst precursor at a temperature between about 150° C. and 300° C. for a period of time between about 1 and 48 hours; (6) compressing the dried catalyst precursor under a pressure of between about 40,000 and 80,000 psi; and (7) calcining the compressed catalyst precursor at a temperature between about 400° C. and 700° C. in a non-reducing atmosphere; wherein the atomic ratio of elements in the catalyst varies between about 0.3 and 2.4 atoms selected from phosphorus, manganese, germanium, zirconium, tin, tellurium, cerium and hafnium, and between about 0.4 and 3.6 atoms selected from titanium, vanadium, niobium, antimony and tantalum, per twelve atoms of molybdenum.

The above-described improved catalyst is highly reactive per se for selective oxidation of olefins to alpha, beta-unsaturated aldehydes and carboxylic acids. In practice, it is advantageous to prepare the selective oxidation catalyst in combination with a carrier substrate such as silica, alumina, silica-alumina, diatomaceous earth, titanium oxide, zirconium oxide, silicon carbide, and any phosphates, silicates, borates, carbonates, and the like, which are stable under the reaction conditions of applications that are contemplated.

Catalyst Preparation

A calculated quantity of ammonium molybdate (e.g., ammonium paramolybdate) is dissolved in distilled water, and ammonium hydroxide is added to adjust the pH to about 8–9.

To the ammonium molybdate solution is added a water-soluble compound which contains an element that functions as a central atom in the formation of a heteropolymolybdate. Illustrative of heteropolymolybdates are $Mo_{16}TeO_x$, $Mo_{12}CeO_x$, $Mo_9PO_x$, and the like Any water-soluble compound(s) containing the essential central atom element can be employed for admixture with the ammonium molybdate solution. Suitable water-soluble compounds include $K_2GeO_3$, $(NH_4)_2TeO_6$, $(NH_4)_2Ce(NO_3)_6$, $(NH_4)_3PO_4$, $Zr(NO_3)_4$, $K_2SnO_6$, $Mn(C_2H_3O_2)_2$, $KMnO_4$, and the like, and mixtures thereof. In a preferred embodiment, hydrogen peroxide is added to the ammonium molybdate solution at the same time that the water-soluble compound is added. As a convenience, the formation of a clear solution of the inorganic compounds can be accelerated by refluxing the admixture until all of the solids are dissolved.

In the next step of the catalyst preparation, to the clear solution described above is added at least one water-insoluble compound of titanium, vanadium, niobium, antimony and tantalum, e.g., $TiO_2$, $V_2O_5$, $Nb_2O_5$, $Sb_2O_3$, $Sb_2O_5$ and $Ta_2O_5$. The pH of the liquid-solid suspension is adjusted into the acid range with a mineral acid. The suspension is stirred to insure thorough mixing, and if desired it can be refluxed for 1-2 hours.

It is particularly preferred to add a finely divided carrier material to the suspension. For example, colloidal silica is an excellent substrate for the invention catalyst composition. The carrier substrate material can be included in the catalyst composition in a quantity between about 5 and 50 weight percent, based on the total weight of the catalyst in final form.

The suspension produced as described above, with or without the carrier component, is reduced to dryness and then heated at temperatures between about 150° C. and 300° C. for a period of time between about 1 and 48 hours. On the average the temperature range is between about 225° C. and 275° C., and the heating time is between 2 and 8 hours. The aqueous phase removal can be effected by conventional procedures such as vacuum distillation, spray drying, tray drying, and the like.

It is usually advantageous to lightly crush the resultant lumpy catalyst precursor solids to more uniform granules for convenience of handling. As a critical aspect of the invention process for catalyst preparation, in the next step the catalyst precursor solids are compressed under a pressure of 40,000 to 80,000 psi. The preferred pressure range for the compression step is between abour 45,000 and 60,000 psi. A less desirable selective oxidation catalyst is obtained if the catalyst precursor is not subjected to a compression step, or if the catalyst precursor is compressed under a pressure less than 40,000 psi or more than 80,000 psi. Excessive pressure is undesirable because it reduces the porosity of the catalyst mass, and adversely affects the level of selective oxidation activity of the catalyst.

As a final step of catalyst preparation, the compressed catalyst precursor composition is calcined at temperatures between about 400° C. and 700° C. for a period of time between about 1 and 36 hours. It is usually preferred to calcine the catalyst composition at a temperature between about 475° C. and 575° C. for a period of time between about 2 and 10 hours in a non-reducing atmosphere. Illustrative of non-reducing atmospheres are air, nitrogen, helium, and the like.

The present invention compressed molybdate catalyst composition is characterized by exceptional crush strength and attrition resistance, as compared to a similar catalyst composition which has not been compressed at a pressure of 40,000-80,000 psi.

Selective Oxidation Process

Illustrative of a preferred selective oxidation process employing a present invention catalyst is the conversion of isobutylene to methacrolein and methacrylic acid.

Suitable reactors for the oxidation of isobutylene include either fixed bed or fluid bed reactors which contain the catalyst of this invention. The gas fed to the reactors is composed of isobutylene and molecular oxygen to which nitrogen, carbon dioxide, steam or the like may optionally be added as an inert diluent. The reaction may be carried out at temperatures ranging from 250° to 500° C., preferably ranging from 350° to 420° C. Though the apparent contact time of the reactants greatly varies according to the reaction temperature and the composition of the feed gas, a range of 0.05 to 20 seconds, preferably a range of 0.4 to 12 seconds, is suitable. The composition of the feed gas may vary over a wide range, but it is preferable to use a feed gas composition which is in the range of 1 to 10 mole percent isobutylene, 20 to 90 mole percent air and 1 to 50 mole percent steam. It is not necessary to use pure oxygen as the source of oxygen. Air is a suitable source of oxygen and is desirable for reasons of economy.

The reactants may be passed over the catalyst, already pre-heated at a temperature close to the reaction temperature or close to room temperature, in which latter case said reactants will heat up rapidly in contact with the catalytic bed, whether it is a fixed or fluidized catalytic bed.

The terms "conversion of isobutylene", "selectivity" and "single-pass yield" which are used herein are defined by the following equations:

$$\text{Conversion of isobutylene} = \frac{\text{moles of isobutylene converted}}{\text{moles of isobutylene fed}} \times 100\%$$

$$\text{Selectivity} = \frac{\text{moles of each product} \times \frac{\text{carbon number of each product}}{4}}{\text{moles of isobutylene converted}} \times 100\%$$

$$\text{Single-pass yield} = \frac{\text{moles of each product} \times \frac{\text{carbon number of each product}}{4}}{\text{moles of isobutylene fed}} \times 100\%$$

The present invention compressed molybdate catalyst composition provides a higher conversion and efficiency of isobutylene to methacrolein and methacrylic acid than does a similar catalyst which has not been compressed at a pressure of 40,000-80,000 psi.

The following examples are illustrative of specific embodiments of the present invention process. As it is apparent to those skilled in the art, in the light of the foregoing disclosure numerous modifications are possible in the practice of this invention without departing from the scope or concept thereof.

EXAMPLE I

A 211.86 gram quantity of $(NH_4)_6Mo_7O_{24}.H_2O$ [ammonium paramolybdate] was dissolved in 400 milliliters of distilled water, and to the solution was added 100 milliliters of conc. ammonium hydroxide solution. Then 31.2 grams of $TeO_2$ and 50 milliliters of 30 percent hydrogen peroxide were added to the solution and the admixture was refluxed overnight. The resulting solution was clear pale yellow in color.

To the solution were added 14.6 grams of $Sb_2O_3$ and 12.8 grams of $Nb_2O_3$. The pH of the liquid-solid suspension was adjusted to 3.5, and then the suspension medium was refluxed for two hours. The pH of the suspension was adjusted to 6 with ammonium hydroxide, and refluxing was continued overnight.

A 200 milliliter quantity of Cabosil M5 silica was added to the catalyst precursor suspension, the pH of the admixture was adjusted to 2±0.5 with nitric acid, and the admixture was homogenized in a blender for 5 minutes.

The resultant slurry was reduced to dryness overnight in a rotor-vaporizer unit. A solid catalyst precursor was recovered and heated in air at 250° C. for 17 hours.

One portion of the catalyst was lightly crushed, and then compressed under 50,000 psi pressure to form wafers of 3 centimeters diameter and 1 centimeter thickness.

The wafers were heated in air from room temperature to 525° C. over a period of 8 hours, held at that temperature for 4 hours, and then cooled to room temperature over the course of 12 hours. Another portion of catalyst, which was not compressed, was subjected to the same calcination schedule.

The oxidation selectivity of the compressed and non-compressed catalysts was compared for the oxidation of isobutylene. Both catalysts were crushed and sieved to 20-30 mesh. A 0.33 inch I.D. reactor was charged with 15 cm$^3$ of catalyst powder for the series of oxidation reaction runs.

The results of the comparative tests are summarized in TABLE I. The test results demonstrated that the compressed catalyst in accordance with the present invention was more highly selective and produced a higher yield of methacrolein and methacrylic acid than did the same catalyst composition which was not compressed.

TABLE I

| Catalyst[1] | Feed, mole % balance in air | | Bath Temp. °C. | Peak Temp. °C. | Contact Time Sec | iC$_4$ Conv % | MA[2] Eff % | MA[2] + MAA[3] | |
|---|---|---|---|---|---|---|---|---|---|
| | iC$_4$ | Steam | | | | | | Yield % | STY g/l/hr |
| Compressed | 3.0 | 38.4 | 375 | 415 | 0.8 | 95.5 | 74.4 | 73.0 | 385 |
| Compressed | 3.0 | 38.6 | 378 | 470 | 0.74 | 96.5 | 70.1 | 69.6 | 362 |
| Compressed | 3.0 | 38.1 | 383 | 467 | 0.54 | 94.0 | 73.0 | 70.6 | 480 |
| Non-compressed | 3.0 | 36.9 | 390 | 411 | .95 | 92.1 | 71.6 | 66.7 | 270 |
| Non-compressed | 3.0 | 39.0 | 397 | 420 | .87 | 93.1 | 67.1 | 63.3 | 268 |

[1]Mo$_{12}$Nb$_1$Sb$_1$Te$_2$O$_x$/SiO$_2$, where x is an integer determined by the oxidation state of the catalyst (e.g., x = 40-47)
[2]Methacrolein
[3]Methacrylic acid

EXAMPLE II

The following catalyst was prepared in the same manner as described above in EXAMPLE I.

A 211.86 gram quantity of (NH$_4$)$_6$Mo$_7$O$_{24}$·4H$_2$O was mixed with water and 100 milliliters of conc. ammonium hydroxide solution. To the solution were added 31.2 grams of TeO$_2$ and 50 milliliters of 30 percent hydrogen peroxide, and the admixture was refluxed until a clear solution formed.

To the solution were added 14.6 grams of Sb$_2$O$_3$ and 12.8 grams of Nb$_2$O$_5$. The pH of the suspension was adjusted to 3.5 with nitric acid, and the medium was refluxed for two hours. The pH was adjusted to 8.5, and refluxing was continued for 64 hours.

A 200 milliliter quantity of Cabosil M5 silica was added. The resultant slurry was homogenized for 5 minutes, and then reduced to dryness in a roto-vaporizer. The solid catalyst precursor was heated in air at 250° C. for 16 hours.

One portion was lightly crushed and compressed under 50,000 psi pressure to wafers. The wafers were heated from room temperature to 500° C. over a period of 8 hours. The temperature was maintained at 500° C. for 4 hours, and the catalyst was allowed to cool to room temperature over a period of 12 hours. The wafers were then crushed to 20-30 mesh. A portion of catalyst that was not compressed was calcined in the same manner.

The oxidation selectivity of the compressed and non-compressed catalysts was compared for the oxidation of isobutylene.

The results of the comparative tests are summarized in TABLE II. The test results demonstrated that a present invention compressed catalyst has superior oxidation selectivity in comparison with a non-compressed catalyst.

TABLE II

| Catalyst[1] | Feed, mole % balance in air | | Bath Temp. °C. | Peak Temp. °C. | Contact Time Sec | iC$_4$ Conv % | MA[2] Eff % | MA[2] + MAA[3] | |
|---|---|---|---|---|---|---|---|---|---|
| | iC$_4$ | Steam | | | | | | Yield % | STY g/l/hr |
| Compressed | 3.0 | 36.9 | 360 | 401 | 1.2 | 87 | 77 | 68 | 200 |
| Compressed | 3.0 | 35.9 | 360 | 392 | 1.2 | 94 | 67 | 64 | 213 |
| Compressed | 3.0 | 35.8 | 365 | 408 | 1.2 | 97 | 68 | 67 | 239 |
| Non-compressed | 3.0 | 36.1 | 380 | 400 | 1.2 | 78 | 58 | 45 | 150 |
| Non-compressed | 3.0 | 36.1 | 385 | 409 | 1.2 | 83 | 66 | 55 | 177 |
| Non-compressed | 3.0 | 36.1 | 390 | 426 | 1.1 | 89 | 67 | 61 | 222 |

[1]Mo$_{12}$Nb$_1$Sb$_1$Te$_2$O$_x$/SiO$_2$, where x is an integer determined by the oxidation state of the catalyst (e.g., x = 40-47)
[2]Methacrolein
[3]Methacrylic acid

What is claimed is:

1. In a process for selectively oxidizing isobutylene to methacrolein and methacrylic acid, the improvement which comprises contacting isobutylene with oxygen in vapor phase in the presence of an oxidation catalyst produced by a method which comprises (1) preparing an aqueous solution of ammonium molybdate; (2) dissolving in the said aqueous solution at least one water-soluble compound of an element selected from phosphorus, manganese, germanium, zirconium, tin, tellurium, cerium and hafnium; (3) admixing with said resulting aqueous solution in (2) at least one water-insoluble compound of a metal selected from titanium, vanadium, niobium, antimony, and tantalum to form a suspension; (4) removing the aqueous phase of said suspension and recovering a solid catalyst precursor; (5) heating said solid catalyst precursor at a temperature between about 150° C. and 300° C. for a period of time between about 1 and 48 hours; (6) compressing the dried catalyst precursor under a pressure of between about 40,000 and 80,000 psi; and (7) calcining the compressed catalyst precursor at a temperature between about 400° C. and 700° C. in a non-reducing atmosphere; wherein the atomic ratio of elements in the catalyst varies between about 0.3 and 2.4 atoms selected from phosphorus, manganese, germanium, zirconium, tin, tellurium, cerium and hafnium, and between about 0.4 and 3.6 atoms selected from titanium, vanadium, niobium, antimony and tantalum, per twelve atoms of molybdenum.

2. A process in accordance with claim 1 wherein the oxygen in the feed mixture is provided as a component of air.

3. A process in accordance with claim 1 wherein the feed mixture contains an inert gaseous diluent.

4. A process in accordance with claim 1 wherein the feed mixture contains steam as an inert gaseous diluent.

* * * * *